United States Patent [19]

Dabrowski

[11] 4,225,732

[45] Sep. 30, 1980

[54] SELECTIVE ORTHO-ALKYLATION OF PHENOLIC COMPOUNDS WITH AN ALKANE IN THE PRESENCE OF A SUPPORTED NICKEL OXIDE CATALYST

[75] Inventor: John E. Dabrowski, Lawrenceville, N.J.

[73] Assignee: General Electric Company, Pittsfield, Mass.

[21] Appl. No.: 863,416

[22] Filed: Dec. 22, 1977

[51] Int. Cl.$^2$ .................. C07C 37/12; C07C 39/06
[52] U.S. Cl. ............................. 568/794; 568/804
[58] Field of Search ............ 260/620, 621 R, 624 C, 260/679 M; 568/780, 744, 804, 794

[56] References Cited

U.S. PATENT DOCUMENTS 3,446,856  5/1969  Hamilton ........................ 260/620
3,716,589  2/1973  Kotanigawa .................. 260/621 R
3,718,704  2/1973  Chapman et al. ................ 260/671

OTHER PUBLICATIONS

Nishizaki et al., Chemistry Letters, pp. 149–150, Chem. Soc. of Jap.
The Van Nostrand Chemist's Dictionary, (1953), pub. Van Nostrand Co., p. 292.
Condensed Chemical Dictionary, (1956) p. 488.

*Primary Examiner*—Werren B. Lone
*Attorney, Agent, or Firm*—Morgan, Finnegan, Pine, Foley & Lee

[57] ABSTRACT

The process of the invention provides a method for the selective ortho-alkylation of a phenolic compound with a lower alkane in the presence of a supported nickel oxide catalyst.

9 Claims, No Drawings

SELECTIVE ORTHO-ALKYLATION OF PHENOLIC COMPOUNDS WITH AN ALKANE IN THE PRESENCE OF A SUPPORTED NICKEL OXIDE CATALYST

This invention provides a process for the selective ortho-alkylation of a phenolic compound with a lower alkane in the presence of a supported nickel oxide catalyst.

BACKGROUND OF THE INVENTION

In Hamilton, U.S. Pat. No. 3,446,856 which is incorporated by reference there is disclosed a method for the selective ortho-alkylation of phenolic compounds. That method is based on the vapor phase reaction of phenol and a lower alkanol in the presence of a magnesium oxide catalyst. The Winkler et al patent, U.S. Pat. No. 2,448,942 discloses an alkylation process whereby penta-substitited phenols are prepared by alkylation of a phenol with a lower alkyl alcohol in the presence of a metal oxide catalyst.

It has been discovered by the applicant that phenols may be selectively ortho-alkylated with a lower alkane by a vapor phase reaction that is carried out in the presence of a supported nickel oxide catalyst. This process is highly selective to the synthesis of 2,6-xylenol. The process may be carried out at ambient pressure and at temperatures below the temperatures mentioned in the above-mentioned Hamilton patent.

Accordingly, it is a primary object of the present invention to provide an improved method for the selective ortho-alkylation of a phenolic compound which is based on the vapor phase reaction of a phenol and a lower alkane.

DETAILED DESCRIPTION OF THE INVENTION

The invention provides a process for the selective ortho-alkylation of a phenolic compound of the formula:

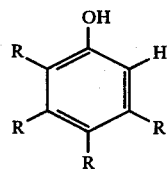

wherein R is a monovalent substituent selected from the group consisting of hydrogen, alkyl, phenyl and alkyl substituted phenyl, said process comprising contacting said phenolic compound with a lower alkane of from 1 to 3 carbon atoms in the vapor phase in the presence of a supported nickel oxide catalyst.

The term alkyl is used to include $C_1$ to $C_{12}$ alkyl groups such as methyl, ethyl, n-propyl, n-butyl, n-hexyl and the like. The term alkyl substituted phenyl is used to include $C_1$ to $C_{12}$ substituted phenyl groups such as 2-methylphenyl, 4-ethylphenyl, 2-n-propylphenyl, 4-n-butylphenyl and the like.

The lower alkanes include methane, ethane and propane.

The preferred phenolic compound is phenol although mixtures of phenols which contain phenols such as phenol and ocresol may be employed.

The nickel oxide catalyst may be supported on any conventional catalyst support such as alumina, silica, kieselguhr, and the like. Magnesium oxide is the preferred support. The catalyst composition should comprise from 1 part by weight to 50 parts by weight of nickel per 100 parts by weight of catalyst composition.

The catalyst may be prepared according to standard techniques. Nickel oxide-magnesium oxide catalysts may be prepared by thermally decomposing mixtures of nickel and magnesium carbonates, or hydroxides that may be prepared by precipitation from mixtures of soluble salts of these metals. The shape of the catalyst may be in the form of pellets, Raschig rings, cylinders, tablets or any shape known to the art.

The catalyst may be employed at a ratio of 0.01 part by weight to 10 parts by weight of nickel to 100 parts by weight of phenolic compounds. Generally, the ratio of lower alkane to phenolic monomer will be from 0.1 parts by weight to 10 parts by weight of lower alkane to 100 parts by weight of phenolic compound although this ratio is not critical. It is preferred to operate the process at ambient atmospheric pressure but if desired pressures of 1 to 20 atmospheres or higher may be employed.

The reaction is carried out in the vapor phase usually with a fixed catalyst bed at a temperature from about 200° to about 500° C. The preferred temperatures for the highly selective production of 2,6-xylenol have been found to be between 325°–370° C.

The reaction may be carried out in the suitable reaction that is useful for vapor phase alkylations. The vapor from the alkylation reaction may be condensed and the reaction products may be separated by crystallization, distillation etc.

DESCRIPTION OF THE PREFERRED EMBODIMENTS

In order that those skilled in the art may better understand the invention, the following example is given by way of illustration and not by way of limitation:

EXAMPLE

A catalyst was prepared by conventional techniques which contained 10% by weight of NiO dispersed on MgO. This catalyst was employed to alkylate phenol with methane. The results were as follows:

| Conversion to 2,6-xylenol | Temperature °C. |
| --- | --- |
| 2.92% | 325° |
| 2.13 | 325° |
| 2.08% | 325° |
| 1.73% | 330° |
| 2.00% | 340° |
| 1.71% | 345° |
| 1.55% | 355° |
| 1.78% | 371° |

Although the above example has shown various modifications and variations of the present invention, other modifications and variations are possible in light of the above teachings. It is therefore to be understood that changes may be made in the particular embodiment of the invention described which are within the full intended scope of the invention as defined by the appended claims.

I claim:

1. A process for the selective ortho-alkylation of a phenolic compound of the formula:

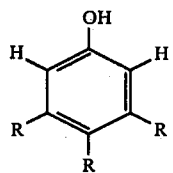

wherein R is a monovalent substituent selected from the group consisting of hydrogen, alkyl, phenyl and alkyl substituted phenyl, said process comprising contacting said phenolic compound with a lower alkane in the vapor phase in the presence of a supported nickel oxide catalyst.

2. A process as defined in claim 1 wherein the lower alkane is methane.

3. A process as defined in claim 1 wherein each R is the phenolic compound is hydrogen.

4. A process as defined in claim 1 wherein the nickel oxide catalyst is supported on a magnesium oxide carrier.

5. A process as defined in claim 4 wherein the process is carried out at atmospheric pressure at a temperature from about 200° to about 500° C.

6. A process as defined in claim 5 wherein the process is carried out at a temperature between 325°–370° C.

7. A process for the selective ortho-alkylation of a phenolic compound of the formula:

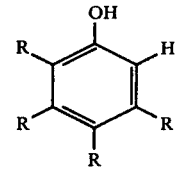

wherein R is a monovalent substituent selected from the group consisting of hydrogen, alkyl, phenyl and alkyl substituted phenyl; said process comprising contacting said phenolic compound with methane in the vapor phase in the presence of a catalyst which consists essentially of nickel oxide supported on magnesium oxide said process being carried out at a temperature of 200°–500° C. and at atmospheric pressure.

8. A process as defined in claim 7 wherein each R is hydrogen.

9. A process as defined in claim 8 wherein the temperature is between 325°–370° C.

* * * * *